United States Patent [19]

Balderson et al.

[11] Patent Number: 5,439,648
[45] Date of Patent: Aug. 8, 1995

[54] GAS INDICATOR FOR A PACKAGE

[75] Inventors: Simon N. Balderson, Telford; Robert J. Whitwood, Stafford, both of United Kingdom

[73] Assignee: Trigon Industries Limited, Auckland, New Zealand

[21] Appl. No.: 249,446

[22] Filed: May 26, 1994

[30] Foreign Application Priority Data

Jun. 3, 1993 [GB] United Kingdom ............... 9311426
Jan. 27, 1994 [GB] United Kingdom ............... 9401557

[51] Int. Cl.6 .................. G01N 33/02; G01N 31/22
[52] U.S. Cl. ........................... 422/86; 422/87; 422/55; 422/56; 422/57; 436/1; 436/3; 436/127; 436/133; 435/31; 435/32; 435/291; 435/810; 426/87; 426/232
[58] Field of Search ............... 422/56, 55, 57, 86, 422/87; 435/31, 32, 805, 810, 291; 436/1, 2, 3, 127, 133, 904; 426/87, 232

[56] References Cited

U.S. PATENT DOCUMENTS

| | | | |
|---|---|---|---|
| 4,003,709 | 1/1977 | Eaton et al. | 23/253 |
| 4,285,697 | 8/1981 | Neary | 23/230 |
| 4,349,509 | 9/1982 | Yoshikawa et al. | 422/57 |
| 4,772,560 | 9/1988 | Attar | 436/165 |
| 4,994,117 | 2/1991 | Fehder | 436/133 |
| 5,320,807 | 6/1994 | Brinton et al. | 422/61 |

FOREIGN PATENT DOCUMENTS

| | | | |
|---|---|---|---|
| 60-252235 | 12/1985 | Japan | G01M 3/20 |
| 4083533 | 7/1990 | Japan | B01J 20/28 |
| 4151554 | 10/1990 | Japan | G01N 31/22 |
| 1492377 | 11/1974 | United Kingdom | G01N 31/22 |
| 2234974 | 2/1991 | United Kingdom | C09J 201/00 |
| WO89/05761 | 6/1989 | WIPO | B65D 55/02 |

Primary Examiner—David A. Redding
Attorney, Agent, or Firm—Christensen, O'Connor, Johnson & Kindness

[57] ABSTRACT

A gas indicator (11) for a modified atmosphere food package (19) comprises a series of strips (12, 13, 14, 15, 16) which progressively change colour as the proportion of carbon dioxide in the atmosphere progressively changes in magnitude due to absorption of the carbon dioxide by the food product (17) over time. The indicator (11) thus is "tuned" to indicate changing atmospheric conditions inside a see-through envelope (10) and thus the condition of the product (17) can be monitored and the package (19) is tamper evident.

14 Claims, 1 Drawing Sheet

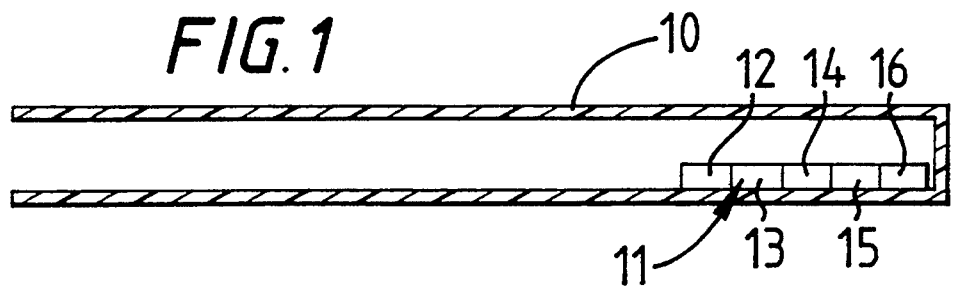
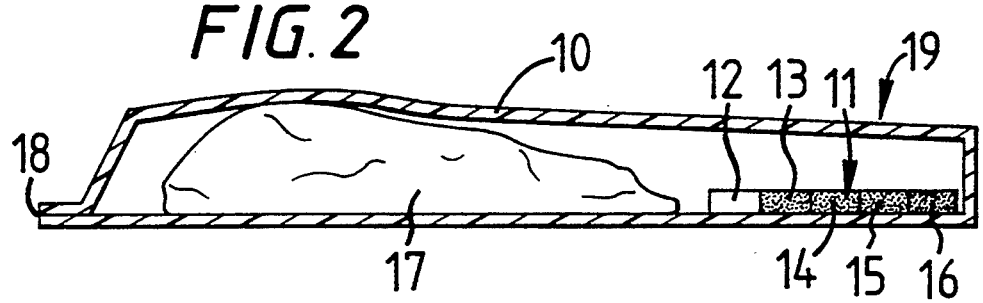
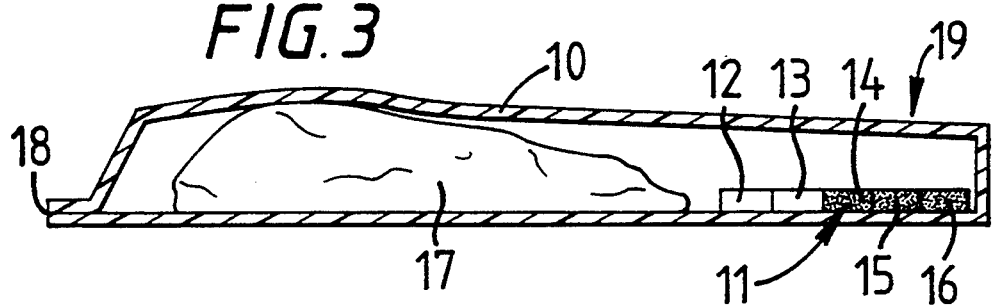
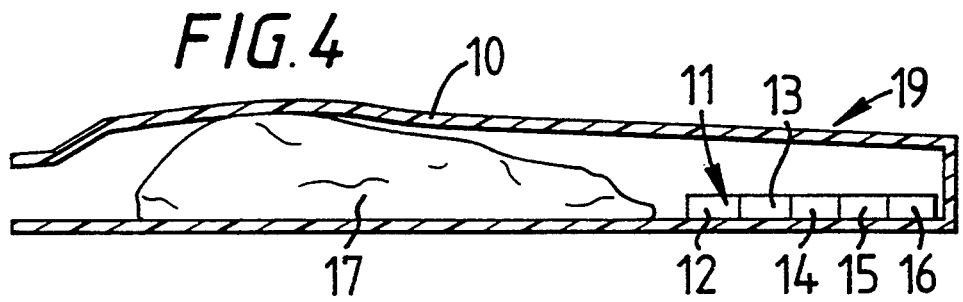

GAS INDICATOR FOR A PACKAGE

FIELD OF THE INVENTION

This invention relates to a gas indicator for a package, and more particularly, to a gas indicator for a package containing a food product in a modified atmosphere contained within the package. Generally, such packaging of food products is referred to as modified atmosphere packaging (MAP).

BACKGROUND OF THE INVENTION

In U.S. Pat. No. 3,899,295 and U.S. Pat. No. 5,096,813 indicator systems are disclosed in which a sensor contained within a package changes colour if the package is tampered with and a gas enters into or escapes from the package. In U.S. Pat. No. 3,899,295 the system provides for the addition of a basic gas to a package before it is closed and a sensor contained within the package changes colour when the basic gas is released if the package is tampered with. In U.S. Pat. No. 5,096,813 the system disclosed includes a sensor contained within the package which changes colour if the package containing no oxygen is tampered with such that oxygen enters into the package.

Although the systems disclosed in U.S. Pat. No. 3,899,295 and U.S. Pat. No. 5,096,813 provide a gas indicator within a package which changes colour when a gas enters in or passes from a package, the systems do not provide for an indication of any change of atmosphere within the package if it is not tampered with.

Furthermore, the system disclosed in U.S. Pat. No. 3,899,295 would not function for MAP because MAP does not involve the addition of a basic gas. The main gas used in MAP is carbon-dioxide, which is acidic. It is the acidity of carbon dioxide used in MAP that provides packaged food with a long shelf life. The addition of a basic gas will offset and ruin this effect.

Similarly, the system disclosed in U.S. Pat. No. 5,096,813 would not be suitable for MAP in which the atmosphere contained in a package included oxygen. More importantly, however, the system is not suitable for MAP because it is not reversible and therefore does not provide the facility for indicating increase and decrease of the proportion of a gas in the atmosphere contained within a package. The system also would be difficult to process because of the short time available during which the sensor material could be exposed to air. Furthermore, the period stated in U.S. Pat. No. 5,096,813 of one to eight hours for colour change of a gas sensor to take effect is much too slow for MAP where it is required that such colour change should be effective within seconds or minutes.

Generally, in MAP an envelope containing a food product is flushed with a specific mixture of gases and the envelope is then sealed. Usually the gases are a combination of carbon dioxide, oxygen and nitrogen, but the atmosphere may consist of only a single gas. For example, red meat is often packaged under a mixture of 20% carbon dioxide and 80% oxygen; poultry is often packaged under a mixture of 25% carbon dioxide and 75% nitrogen; cheese is often packaged under 100% carbon dioxide; and fresh pasta is often packaged under 100% nitrogen.

A problem with MAP is that it is difficult to ensure that a correct gas mixture is provided in a package. Generally, screening is carried out by testing a small percentage of a batch of packages and, if any of the tested packages are found to be defective, the whole batch of packages is discarded including many untested and satisfactory packages included in the batch. More importantly, there is no indication that and atmosphere initially established is still present in a package. If the package is opened or tampered with and gases contained therein escape, generally the first indication that the package is defective is when the product shows signs of deterioration.

SUMMARY OF THE INVENTION

According to the present invention there is provided a food package comprising a sealed envelope and a food product contained in the envelope characterised in that there is also contained in the envelope an indicator adapted to change colour when a gas in the envelope is of a predetermined magnitude.

The indicator thus provides immediate warning if an atmosphere inside the package changes.

BRIEF DESCRIPTION OF THE DRAWINGS

Following is a description, by way of example only and with reference to the accompanying drawings, of one method of carrying the invention into effect.

FIG. 1 is a diagrammatic representation of a flexible container for a package in accordance with the present invention, the container being shown in an open condition prior to insertion of a food product therein, FIG. 2 is a diagrammatic representation corresponding to FIG. 1 showing the container containing a food product, the container having been gas flushed and sealed to form a package, FIG. 3 is a diagrammatic representation corresponding to FIG. 2 in which an indicator in the package indicates a change in the concentration of carbon dioxide contained within the package compared with the situation representated in FIG. 2, and FIG. 4 is a diagrammatic representation corresponding to FIGS. 2 and 3 showing the package in an opened condition.

DETAILED DESCRIPTION OF THE PREFERRED EMBODIMENT

Referring now to the drawings, there is shown a flexible container 10 formed of transparent plastics film material having print information (not shown) printed on an outer surface thereof. The container 10 has located therein an indicator 11 comprising a series of strips 12, 13, 14, 15 and 16 each of which is adapted to change colour as the proportion of carbon dioxide contained within the container 10 changes, the colour change being graded from the first strip 12 to the last strip 16 in the series as the concentration of carbon dioxide within the container 10 decreases in predeterrmined stages of magnitude, for example 25%; 20%; 15%; 10% and 5%. The indicator 11 may be adhesively applied to an inner surface of the container 10 and may comprise a label. Alternatively the indicator 11 may be formed by printing gas sensitive ink on an inner surface of material which is formed into the container 10.

The container 10 is adapted to receive a food product 17 and, subsequent to the food product 17 having been inserted in the container 10 the container 10 is gas flushed, closed and sealed, as shown at 18. The combination of the container 10, the food product 17 and the gas flushed atmosphere contained within the container 10 provides a food package 19. The indicator 11 may be covered by a gas permeable membrane (not shown) so as to separate the indicator 11 and the food product 17 from contact one with another.

The proportion of the carbon dioxide in the package 19 would be indicated by a change of colour of one or more of the strips 12 to 16. In FIG. 2 for example only the strip 12 has changed colour. The colour change will have been "tuned" to the category of food product 17 of the package 19. In red meat packaging for example, only the first strip 12 of the indicator 11 would have changed colour if the proportion of carbon dioxide in the atmosphere in the package remained stable at 25%, as indicated in FIG. 2 of the drawings.

It is known that food products generate or absorb gases when the products degenerate. In the food package 19, absorbtion of carbon dioxide by the food product 17 during storage results in a change in the proportion of carbon dioxide contained in the atmosphere in the container 10 as a result of which one or more of the remaining strips 13 to 16 of the indicator 11 would change colour, as indicated in FIG. 3 of the drawings. The condition of the food product 17 contained within the container 10 thus can be monitored by colour changes of the strips 12 to 16 of the indicator 11 viewed through the material of the container 10.

Clearly if the package 19 is opened, as shown in FIG. 4, there will be a complete change of atmosphere within the container 10 which will be reflected by colour change of all of the strips 12 to 16 of the indicator 11. The indicator 11 thus provides a tamper evident system for the food package 19.

An example of a carbon dioxide sensitive indicating material for providing the indicator 11 is disclosed in WO 91/05252.

It will be appreciated that a change of colour of the strips 12 to 16 of the indicator 11 when the package 19 is opened is a guarantee of correct packaging and storage to the consumer and change of colour of the indicator 11 when the package 19 is initially sealed is a guarantee of correct gas flushing to the packager.

Furthermore, it will be appreciated that colour change of the indicator 11 is reversable so that the indicator 11 indicates both correct filling and subsequent opening.

The provision of an indicator 11 in which colour change is reversible ensures that packaging of food products 17 can be effected in normal ambient conditions and without any time constraints which would otherwise be necessary if the indicator 11 were not reversible and could only be exposed to air for a limited period without there being irreversible colour change.

It will alo be appreciated that the indicator 11 may be such that colour change results when in the presence of a gas other than carbon dioxide. For example, the indicator 11 may change colour according to the level of or in the presence of oxygen.

We claim:

1. A food package (19) comprising:
   a sealed envelope (10) containing a food product (17);
   a predetermined ratio of gases inserted into the envelope (10) prior to sealing; and
   an indicator (11) which changes color when there is a change in the concentration of at least one gas of said ratio and further changes color when the sealed envelope (10) is opened.

2. The package (19) as claimed in claim 1, wherein the indicator (11) is applied to an inner surface of the envelope (10).

3. The package (19) as claimed in claim 2, wherein the indicator (11) is a label.

4. The package (19) as claimed in claim 2, wherein the indicator (11) comprises material primed on the said inner surface.

5. The package (19) as claimed in any one of the preceding claims, wherein the indicator (11) is protected from the product (17) by means of a gas permeable membrane.

6. The package (19) as claimed in claims 1, 2, 3, or 4, wherein said at least one gas is carbon dioxide.

7. The package (19) as claimed in any one of claims 1-4, wherein said at least one gas is oxygen.

8. The package (19) as claimed in claim 5, wherein said at least one gas is carbon dioxide.

9. The package (19) as claimed in claim 5, wherein said at least one gas is oxygen.

10. A food package (19) comprising:
    a sealed envelope (10) containing a food product (17);
    a predetermined amount of gas inserted into the envelope (10) prior to sealing; and
    an indicator (11) which changes color when there is a change in the concentration of said gas and further changes color when the sealed envelope (10) is opened.

11. The package (19) as claimed in claim 10, wherein the indicator (11) is applied to an inner surface of the envelope (10).

12. The package (19) as claimed in claim 11, wherein the indicator (11) is a label.

13. The package (19) as claimed in claim 11, wherein the indicator (11) comprises material printed on said inner surface.

14. The package (19) as claimed in any one of claims 10-13, wherein the indicator (11) is protected from the product (17) by means of a gas permeable membrane.

* * * * *

UNITED STATES PATENT AND TRADEMARK OFFICE
CERTIFICATE OF CORRECTION

PATENT NO. : 5,439,648
DATED : August 8, 1995
INVENTOR(S) : S. N. Bladerson et al It is certified that error appears in the above-indentified patent and that said Letters Patent is hereby corrected as shown below:

COLUMN      LINE

[56]      Refs. Cited      Insert --3,899,295  8/1975  Halpern--

[56]      Refs. Cited      Insert --5,096,813  3/1992  Krumhar et al.--

4            19          "primed" should read --printed--
(Claim 4,  line 2)

Signed and Sealed this

Fifth Day of December, 1995

Attest:

BRUCE LEHMAN

Attesting Officer

Commissioner of Patents and Trademarks